United States Patent [19]

Bellotti et al.

[11] Patent Number: 4,882,496

[45] Date of Patent: Nov. 21, 1989

[54] APPARATUS FOR EXCHANGING AND IRRADIATING TUBING CONNECTIONS

[75] Inventors: Marc Bellotti, Libertyville; Arthur Lueders, Mundelein; Daniel B. Granzow, Ingleside; Larry C. Taylor; Mark Nauman, both of McHenry, all of Ill.

[73] Assignee: Baxter International Inc., Deerfield, Ill.

[21] Appl. No.: 188,012

[22] Filed: Apr. 29, 1988

[51] Int. Cl.$^4$ .............................................. A61L 2/10
[52] U.S. Cl. .................................... 250/455.1; 604/29
[58] Field of Search ............... 250/455.1, 454.1, 492.1; 604/28, 29

[56] References Cited

U.S. PATENT DOCUMENTS

| | | | |
|---|---|---|---|
| 2,249,473 | 7/1941 | Jackson | 250/454.1 |
| 4,433,244 | 2/1984 | Hogan | 250/455.1 |
| 4,448,750 | 5/1984 | Fuesting | 250/455.1 |
| 4,475,900 | 10/1984 | Popovich et al. | 604/28 |
| 4,500,788 | 2/1985 | Kulin et al. | 250/455.1 |
| 4,503,333 | 3/1985 | Kulin et al. | 250/492.1 |
| 4,620,845 | 11/1986 | Popovich et al. | 604/28 |
| 4,655,753 | 4/1987 | Bellotti et al. | 604/29 |
| 4,774,415 | 9/1988 | Biegel et al. | 250/455.1 |

*Primary Examiner*—Bruce C. Anderson
*Attorney, Agent, or Firm*—Charles R. Mattenson; Paul C. Flattery

[57] ABSTRACT

Apparatus for disconnecting, sterilizing and making new tubing connection. The apparatus includes electromechanical means for sensing the presence of a clamp to prevent fluid leaks during operation. The apparatus also includes means for forcing compliance with a predetermined sequence of operations. All electronic components are contained in the top of the apparatus to isolate same from any potential fluid leads which will naturally flow over and into the base of the apparatus.

5 Claims, 8 Drawing Sheets

APPARATUS FOR EXCHANGING AND IRRADIATING TUBING CONNECTIONS

FIELD OF THE INVENTION

The invention is an apparatus for breaking connections between various flow conduits or tubings and making new such connections which are sterile. It applies particularly in medical applications, for example peritoneal dialysis.

DESCRIPTION OF THE PRIOR ART

In various fields of medicine and elsewhere, and particularly in continuous ambulatory peritoneal dialysis (CAPD), there is a need to make and break connections between peritoneal tubing communicating with the peritoneal cavity and a source of peritoneal dialysis solution with substantially sterile procedure. At the same time it is desirable for patients undergoing CAPD or another form of peritoneal dialysis on a chronic basis to be released from close supervision by medical personnel and permitted to do the dialysis solution exchange procedures independently at their homes or places of work. However, the need for maintenance of substantially sterile procedure remains critical if peritonitis is to be avoided, particularly in the case of patients on CAPD.

In response to this, various systems for irradiation of connectors have been proposed, and some have been commercially developed, in which at least the outer connector is made of ultraviolet transparent material, and after the connectors are brought together but before seals are released to permit flow of solution through the newly formed connection, the connectors are irradiated with ultraviolet light for antibacterial effect outside and inside the connectors. See Popovich and Moncrief Pat. Nos. 4,475,900 and 4,620,845 entitled "METHOD OF PERITONEAL DIALYSIS IN ULTRAVIOLET RADIATION OF DIALYSIS APPARATUS"; Kulin et al. U.S. Pat. No. 4,412,834, entitled "ANTIMICROBIAL ULTRAVIOLET IRRADIATION OF CONNECTOR FOR CONTINUOUS AMBULATORY PERITONEAL DIALYSIS" and Hogan Pat. No. 4,433,244, entitled "APPARATUS FOR IRRADIATING TUBING CONNECTIONS". In all of the three U.S. patents, ultraviolet radiation is used for antibacterial effect in the newly formed connection.

Patients who are undergoing peritoneal dialysis on a chronic basis are often elderly, ill, and debilitated. The disease which requires their life maintenance by dialysis interferes with nerve conductivity which, in turn, reduces their manual dexterity. Accordingly, it becomes desirable in the case of many patients to provide them with all assistance possible in the making and breaking of connections during peritoneal dialysis and particularly CAPD operations.

In response to this, automatic systems for making and breaking connections have been provided. For example, the Steri-Track device which has been used and which is described in an article entitled "CAPD For the Blind" from the periodical Nephrology Nurse, March/April, 1981, pp. 53-54. This device is a self-contained portable device. When doing bag exchanges, a fresh bag of dialysate is placed into a stationary end of a holder. At this point the protective tab of the bag is removed, and a spike is taken from the discharge bag and fitted into the grooves of a sliding plate. The patient now manipulates the sliding plate toward the bag with the result that the spike will plunge into the port of the bag with alleged 98 percent probability.

Also, Munsch et al. patent application No. 416,785, filed Sept. 10, 1982, now abandoned, shows an improved device for automatic connection and disconnection of connectors in CAPD and the like.

Another such device providing automatic connection and disconnection of connectors in CAPD and the like is disclosed in U.S. Pat. No. 4,655,753 to Bellotti et al. The device shown therein automatically uncouples two connectors and forms a new coupling between one of the connectors and another connector in an aseptic manner, without contamination from the user through handling.

While the inventions disclosed in the above referenced patents and publications do embody significant improvement over the connection and disconnection of tubing connectors by hand, and the manual application thereto of some sort of antiseptic agent such as iodine, significant shortcomings still exist. For example, the irradiation apparatus disclosed in U.S. Pat. No. 4,433,244 is extremely susceptible to breakdown due to fluids leaking from the tubes or connections into the electronic components. It must be remembered that many of the fluids employed in the various medical applications are electrolytic and therefore tend to promote corrosion. The various connection devices are also susceptible to leaks or spills in that no provision is made for insuring that the tubing being connected is empty or clamped off before the connection is made. Similarly, no provision is made for insuring that the exchange process, once begun, is completed and not interrupted or reversed, such as by disoriented or simply physically debilitated patients.

These and other short comings in the prior art are for the first time even recognized, and met in the present invention as described below.

SUMMARY OF THE INVENTION

In accordance with the present invention, an improved apparatus for exchanging tubing connections, i.e. making and breaking connections between connectors, and irradiating the connectors for antimicrobial effect, is provided. The apparatus of the present invention achieves almost foolproof operation by a user with minimal effort, maximal reliability, and virtual elimination of fluid leaks. In the extremely rare event of a fluid leak, all electronic components are maintained out of the path of the leak and extreme ease and efficiency of cleaning and service is achieved.

One factor in the vast improvement in reliability, cleaning and service achieved over prior art designs is the use of a housing for the apparatus having top and bottom portions removably attached to one another with all electronic components located in the top portion of the apparatus. All fluid connections rest in fittings located on the bottom portion of the apparatus. This removes all electronic components from the natural paths of flow of accidental fluid leaks.

Furthermore, since the bottom portion of the housing contains only mechanical components, and the two portions are removably attached, the bottom portion is readily detached from the top portion and easily cleaned by the user. The substantial improvements in ease of maintenance, as well as the economies achieved by the vastly improved reliability over the prior art apparatus cannot be overemphasized.

The apparatus of the present invention also includes for the first time in any device of this kind, means for preventing operation of the apparatus if there is fluid in the connection which might escape when the connection is broken. More specifically, the apparatus employs novel means for sensing the presence of a clamp on the tubing which, if not present, would allow fluid to escape tube before reconnection. If the presence of an appropriate clamp is not detected, the apparatus does not allow the tubing disconnection to be made or any subsequent steps in the procedure. This feature of the present invention clearly adds another substantial safeguard to prevent leaks or spills which could otherwise take an absolutely essential piece of apparatus out of service by a patient and thereby possibly create a life threatening situation within a matter of hours.

The present invention, in a further very substantial improvement over anything in the prior art, also includes means for forcing compliance. In other words, the apparatus functions to break one connection between two fluid connectors, irradiate the connector to be reused for antibacterial effect, and then make a second connection between the now sterile reused connector and a fresh sterile connector on a new fluid supply. The complete function of the apparatus takes place through a strict predetermined sequence of steps which the user must not deviate from. To ensure that no mistakes are made, the apparatus includes means including the clamp sensing means described above, to ensure that the tubing is properly placed and empty before the operations of the apparatus are begun, and, once begun, that the sequence cannot be deviated from by the user.

Again, the importance of such features cannot be over emphasized. It must be borne in mind that many patients who would be in need of such an apparatus, i.e. those requiring constant and/or long term administration of fluids, such as those on continuous ambulatory peritoneal dialysis, are often substantially physically debilitated. They would have great difficulty, if not find it impossible, to summon the manual dexterity required to make and break these tubing connections in an antiseptic and efficient manner multiple times daily without the apparatus of the present invention.

DETAILED DESCRIPTION OF THE PREFERRED EMBODIMENTS

Figure 1:
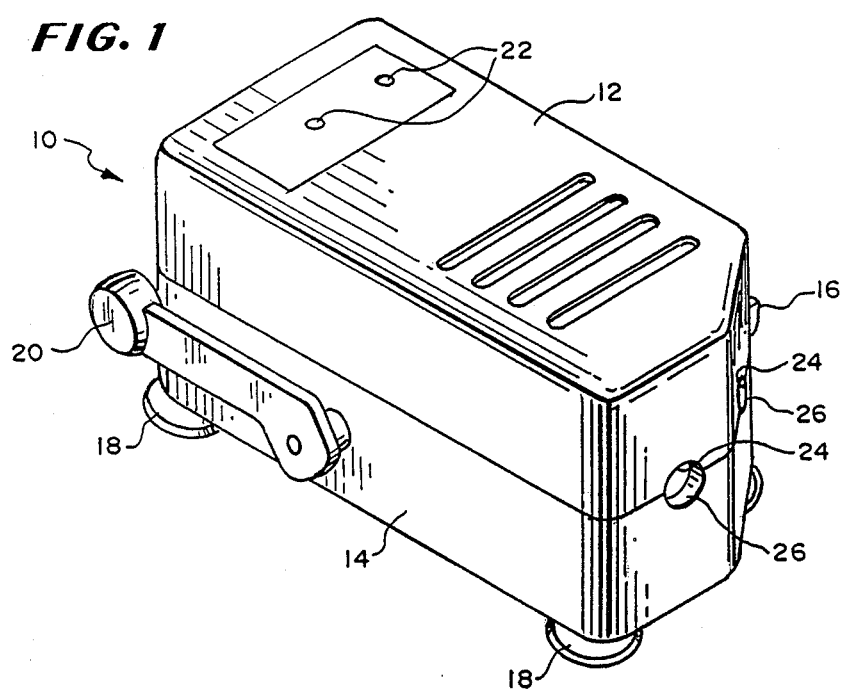
FIG. 1 is a perspective view of the apparatus of the present invention.

The apparatus 10 of the present invention is shown in FIG. 1. It includes a top or cover 12 and a base or lower portion 14 preferably joined by removable means such as hinge 16. Apparatus 10 may include rubber feet or suction cups 18 and has a handle 20 for operation by the user or patient as described below. The apparatus 10 also includes two indicators 22, such as light emitting diodes, which indicate the status of the operation of apparatus 10 as described further below. Cover 12 and base 14 also have corresponding slots 24 and 26 which cooperate as shown to provide paths for the connectors to be connected and disconnected by apparatus 10.

Figure 2:
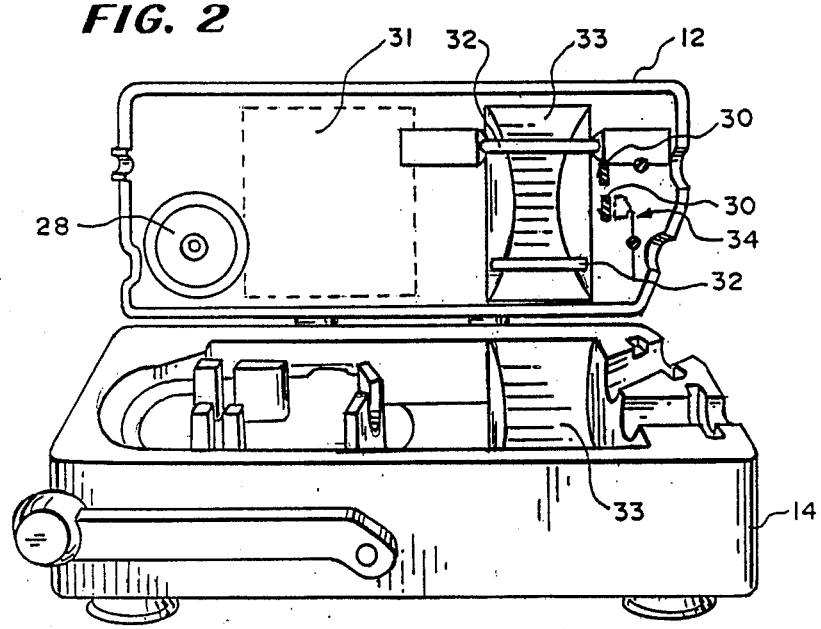
FIG. 2 is a perspective view of the inside of the apparatus of the present invention.
Figure 7:
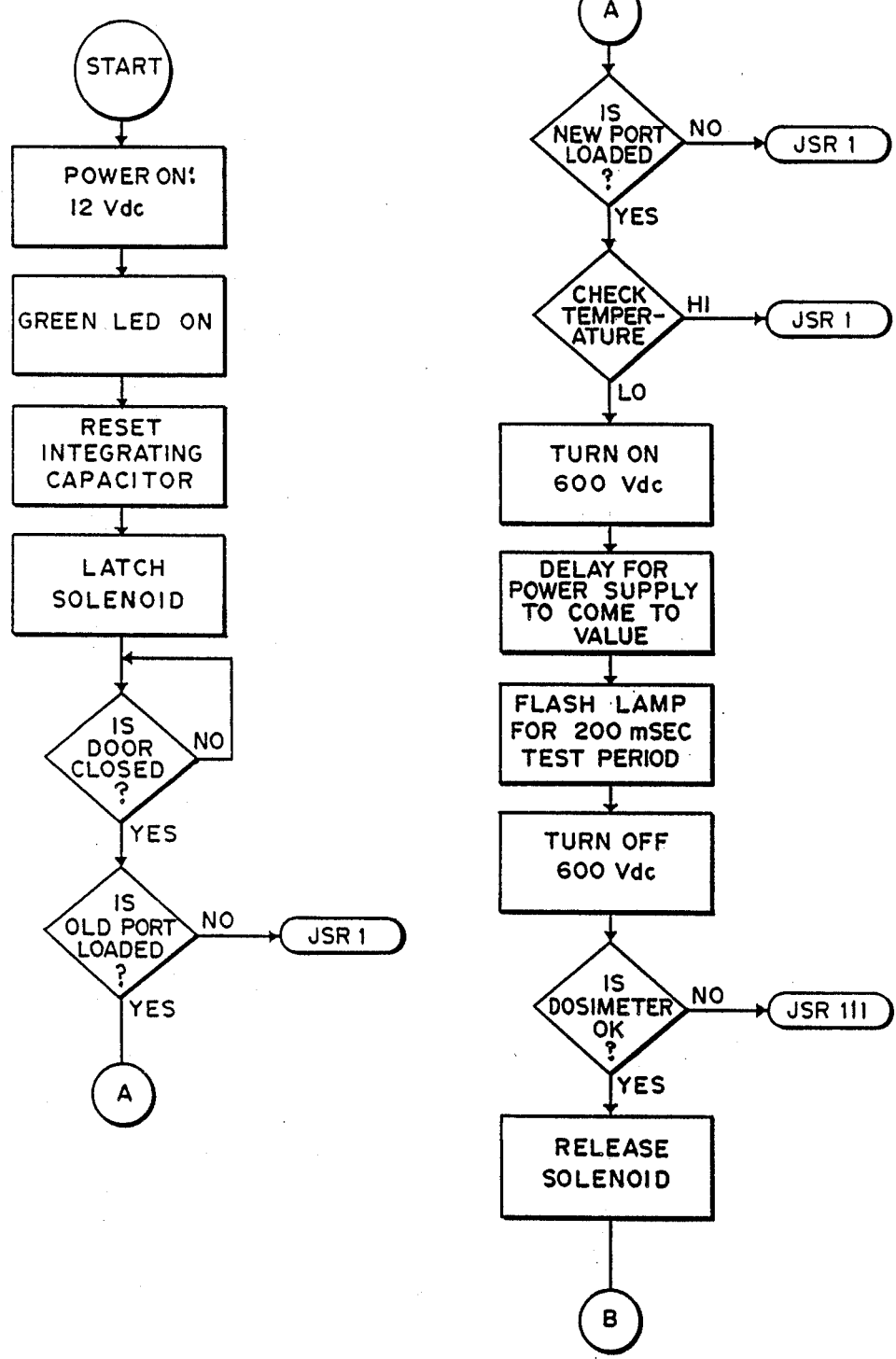
FIGS. 7 and 8 are block diagrams describing the logic functioning of the circuit of FIG. 6.
Figure 8:
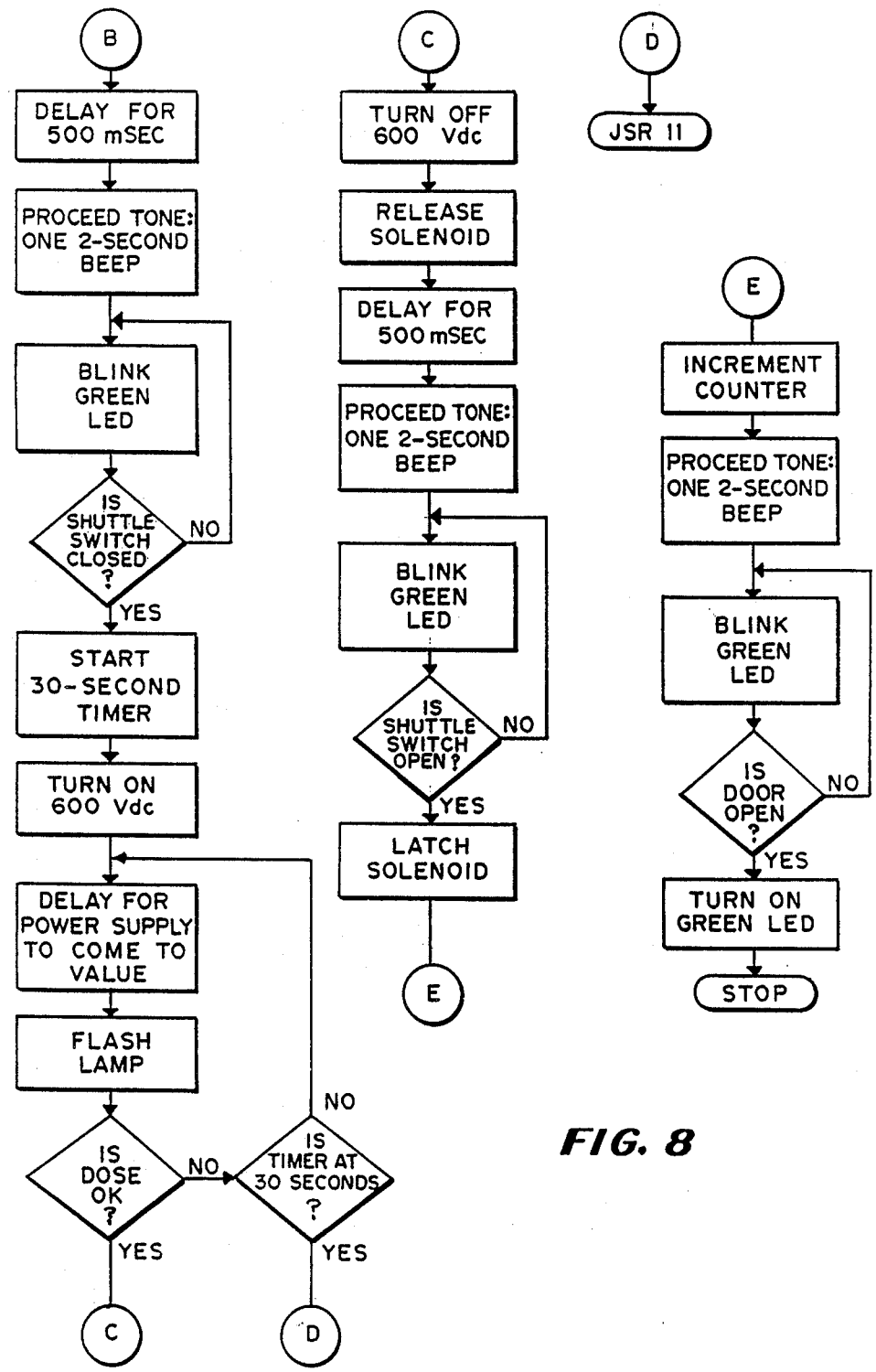
Figure 9:
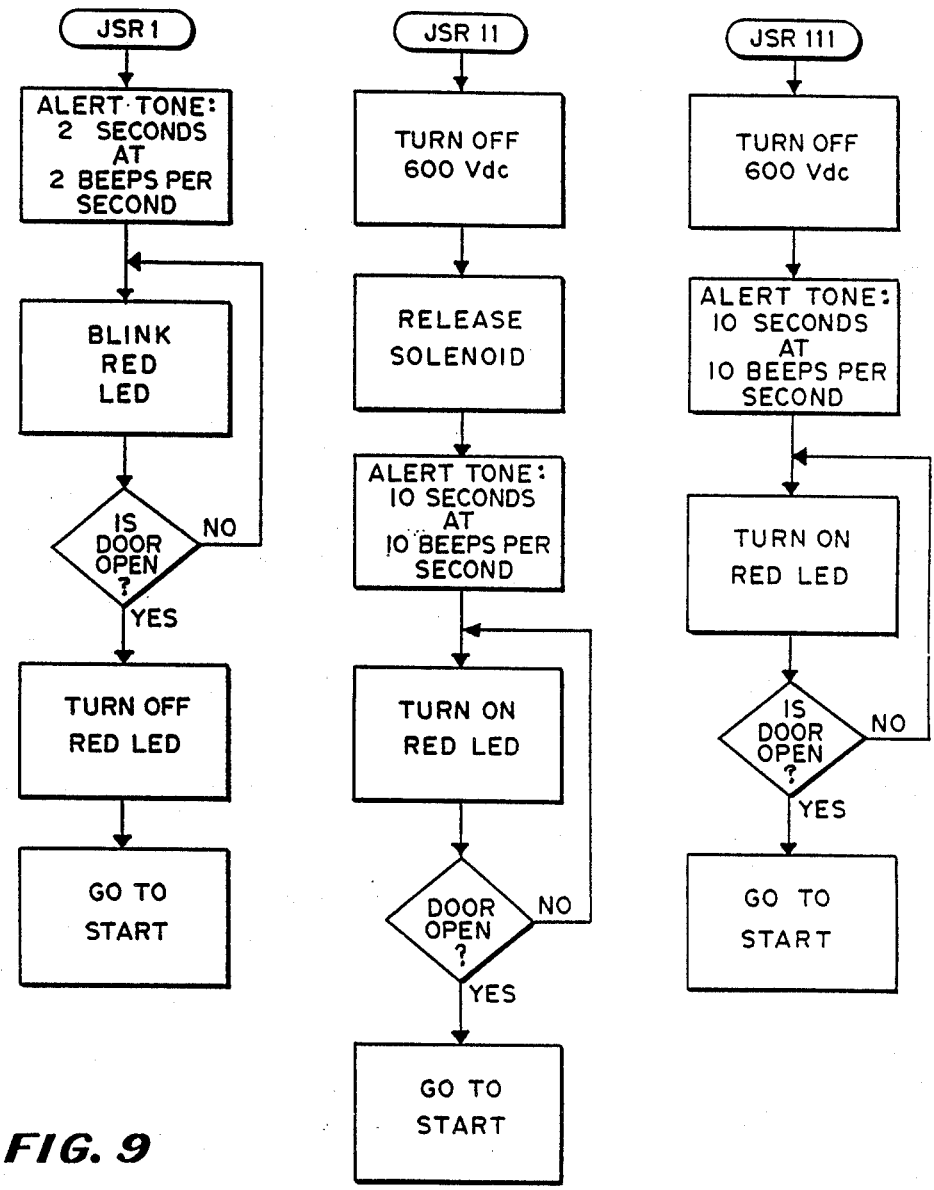
FIG. 9 is a block diagram describing the function of subroutines (JSR) I, II and III of FIGS. 7 and 8.

Referring now to FIG. 2, all electronic components of the apparatus 10 are located in cover 12. These include a solenoid 28, Hall Effect sensors 30 and circuitry 31, which preferably take the configuration illustrated in FIG. 6 and functions as schematically set forth in FIGS. 7 through 9. Cover 12 also houses radiation sources for antimicrobial effect, such as ultraviolet emitting lamps 32 appropriately arranged within reflectors 33, located in both the cover 12 and base 14. One preferred type of ultraviolet lamp which could be used in the apparatus of the present invention is a flash discharge lamp containing a rare gas such as xenon. Such a UV lamp is disclosed in U.S. Pat. No. 4,464,336 to Hiramoto. The inventors have found the use of elliptical reflectors to be advantageous in the preferred embodiment to effectively focus the radiation produced by lamps 32 on the connectors.

FIGS. 1, 2, 4 and 5 illustrate a preferred embodiment of the clamp sensing mechanism 34 of the apparatus 10. In this embodiment, mechanism 34 is an electromagnetic/mechanical mechanism including a carrier arm 36 which is mounted such that the arm 32 is held over one of the upper slots 24 and which at its free end 38 carries a magnet 40. Arm 36 is preferably spring-biased downward so that it extends below the upper edge of the slot 24. Mechanism 34 functions as follows.

Figure 5:
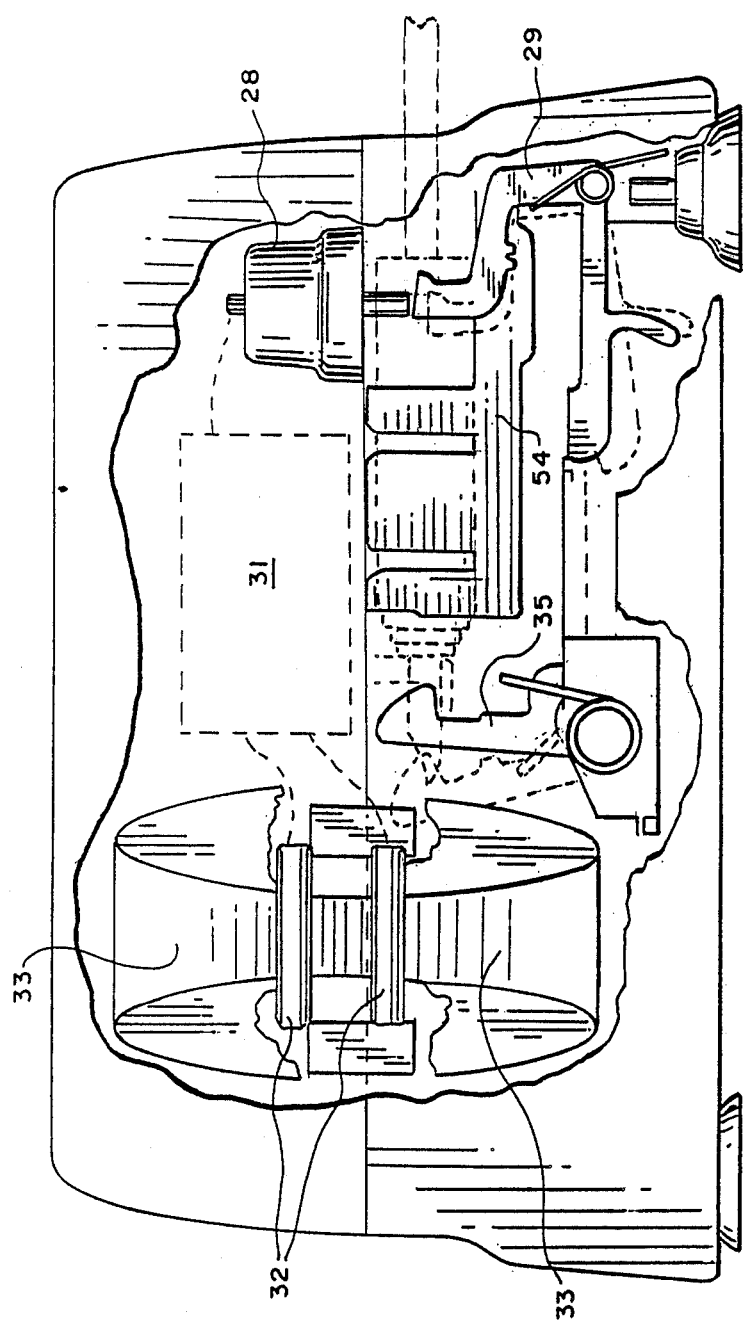
FIG. 5 is a partial broken away side view of the apparatus of FIG. 1.

When a connector with appropriate clamp is inserted into the hole formed by corresponding slots 24 and 26 under arm 36 when the cover 12 and base 14 of apparatus 10 are closed, arm 36 is raised against its bias until magnet 40 lines up with the now adjacent Hall Effect sensor 30 and thereby causes a signal to flow through the circuitry 32 to solenoid 28 which trips spring biased arm 29 which articulates with latch 35 as shown in FIG. 5, and allows handle 20 to be thrown by the patient. This locks the cover 12 and base 14 of apparatus 10 closed and begins the forced compliance with the entire sequence of operations as explained in greater detail below.

If a proper sized clamp is not present within the hole formed by the corresponding slots 24 and 26, indicating the possibility of fluid within the tubes to be disconnected, arm 36 will not be raised against the bias of spring 42 a sufficient amount to bring magnet 40 into alignment with the immediately above Hall Effect sensor 30. Therefore, a signal will not be sent to throw the solenoid 28, handle 20 will remain locked in its starting position, the cover 12 and base 14 portions will not be locked in the closed position and the sequence of operations of the apparatus 10 will not be allowed to begin. In this way, the problem of fluid leaks, which is not even contemplated in the prior art, is effectively dealt with.

Figure 3:
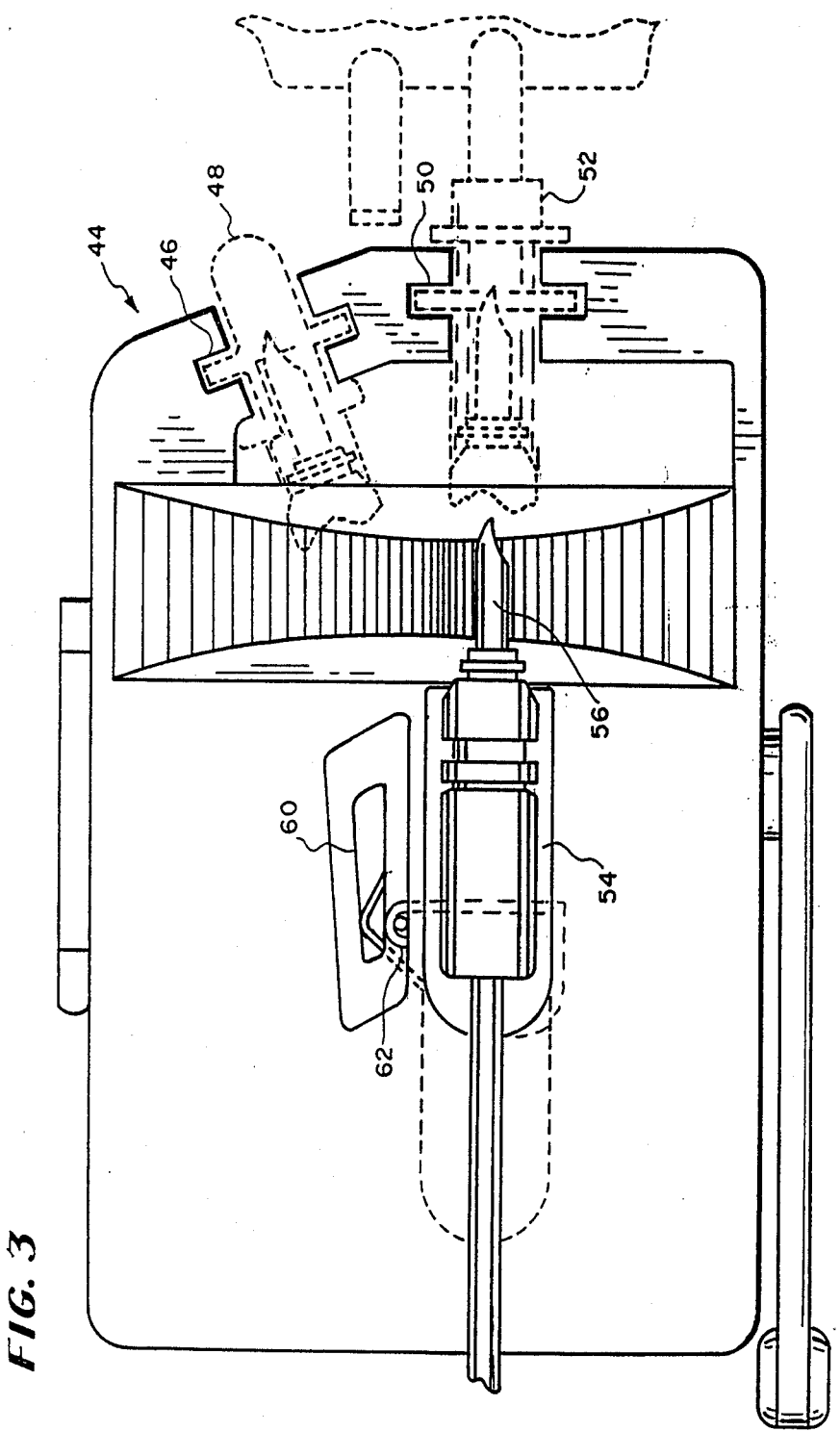
FIG. 3 is a top view of the bottom portion of the apparatus of the present invention.
Figure 4:
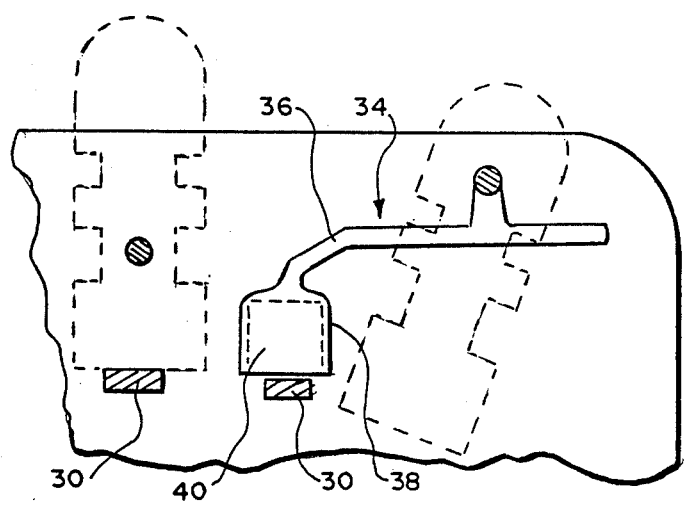
FIG. 4 is a detail view of the clamp sensor mechanism of the present invention.

Referring now more particularly to FIG. 3, the essential mechanism of exchange means 44 for connecting and disconnecting tubing connections is shown. The mechanism contemplated by the inventors is essentially that disclosed and claimed in the aforementioned U.S. Pat. No. 4,655,753 issued Apr. 7, 1987 for a CONNEC- TION DEVICE and which is assigned to the assignee of the present invention and incorporated herein by reference.

As shown therein and in FIG. 3, exchange means 44 includes a first holder 46 for holding a first connector or cap 48, a second holder 50 for holding a second connector or cap 52 and a third holder 54 for holding a third connector 56 capable of mating with either of connectors 48 or 50. Third holder 54 is movable between a first advanced position adjacent first holder 46 (shown in phantom in FIG. 3), a second advanced position adjacent second holder 50 (shown in phantom in FIG. 3) and a retracted position away from both of holders 46 and 50.

One improvement contemplated by the inventors of the present invention over the disclosure of U.S. Pat. No. 4,655,753 is the addition of cam 60 and cam follower 62 contained within base 14 which, as may be readily ascertained from FIG. 3, function to prevent the third holder 54 from being shifted to a position ready for advancement to the second position until it is completely retracted from the first position, i.e. until third connector 56 is completely removed from first connector 48.

Figure 6:
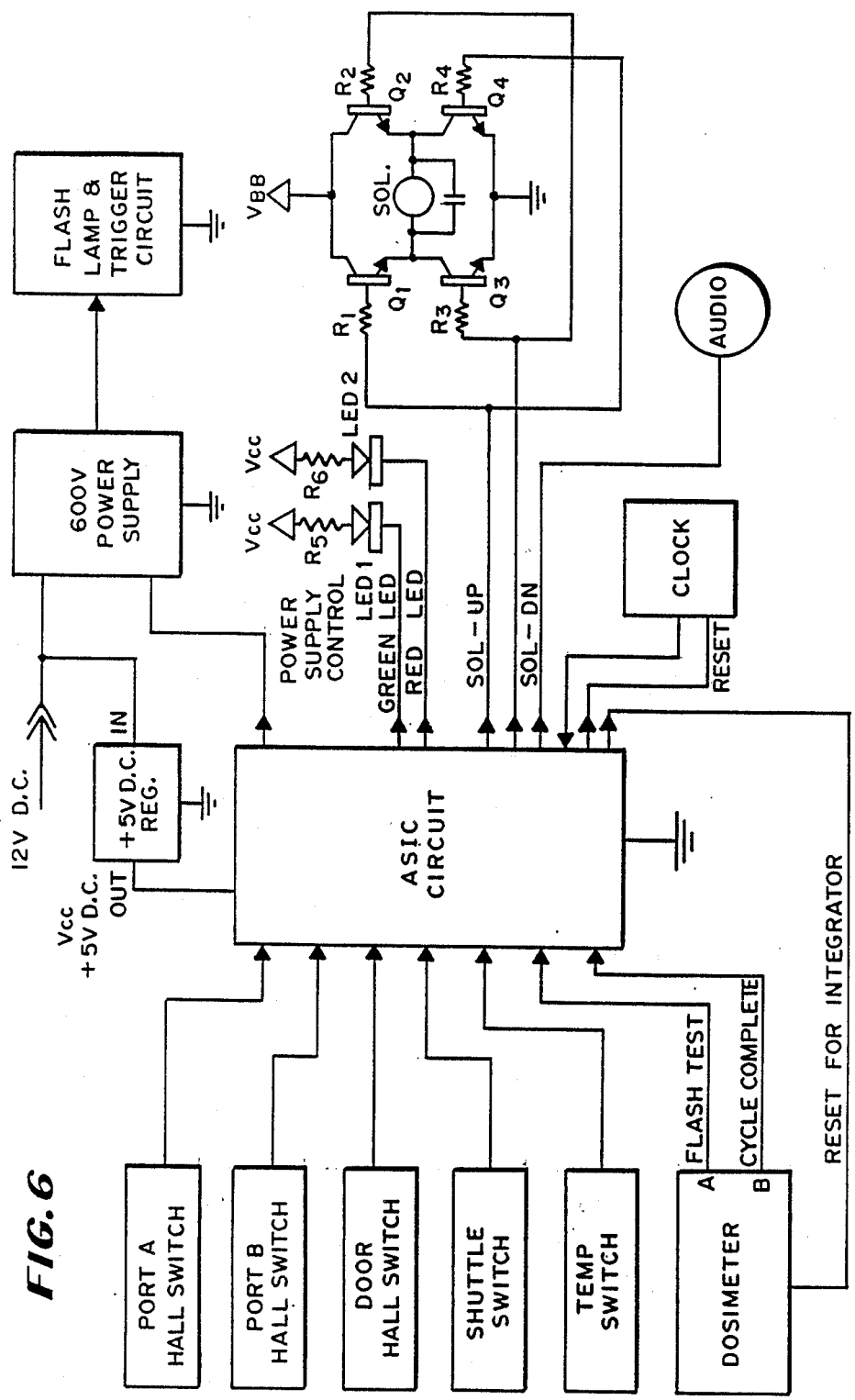
FIG. 6 is a circuit diagram of the logic circuit which controls the apparatus of the present invention.

FIG. 6 illustrates the essential electronic connections and functioning of the apparatus 10 as described herein. The circuit, which is mostly self-explanatory, includes an application specific integrated circuit (ASIC) which performs the functions outlined in FIGS. 7 through 9.

With respect to FIGS. 6–9, the apparatus 10 functions as follows:

1. Once connected to power, the green LED turns on and circuits will be checked. This will assure the user that power has indeed been connected to the device.
2. The cover is opened by pushing the handle to the full forward position. The tubing connection to be broken is loaded into the first holder. The new connector to be used in the new sterile connection is loaded into the second holder.
3. The cover is closed and latched.
   a. The cover and door sensing switches, and the clamp sensing mechanisms must all sense the appropriate conditions, i.e. that the top is closed and latched and the appropriate clamps are in place, to start the procedure.
   b. If either the old or the new connector is missing, the red LED blinks continuously and the procedure error alarm sounds for two seconds at the rate of two beeps per second.
   c. If the condition described in 3a is satisfied, the temperature is first tested to assure its within a safe range. If the temperature is outside the predetermined limits, the procedure error alarm will sound for two seconds at the rate of two beeps per second and the red LED will blink continuously until the temperature has dropped to within acceptable limits.
   d. If the temperature is within the safe range, a second test is performed to actuate the dosimeter to assure that it is functioning properly. This may be done by sensing that the amplitude of a single flash of the UV lamps is within predetermined limits. If the dosimeter is not within acceptable limits, the system error alarm sounds for ten seconds at a rate of ten beeps per second and the red LED turns on continuously, which represents a system failure mode. The failure cycle can be confirmed by opening and closing the cover a second time. If a failure is not detected, the procedure can continue.
   e. If both the temperature and the dosimeter are within acceptable limits, the green LED blinks continuously, the audible indicator sounds continuously for two seconds, and the solenoid is pulsed to unlock the carriage for moving the third holder.
4. The patient pulls the handle to the back position (pointing away from the old and new connectors).
   a. The shuttle mechanism carrying the third holder 54 backs up, breaking the connection with the old connector and retreating to the retracted position. This is also the position in which the radiation sterilization of third connector 56 is effected as it is now being held within the elliptical reflectors, as illustrated in FIG. 3.
   b. The green LED turns off.
   c. The solenoid is pulsed to lock the carriage holding the holder and third connector 56 in position.
   d. The UV lamps operate to sterilize the connector.
   e. The dosimeter monitors the application of the UV light and terminates the flashing when acceptable limits are met. If an acceptable dosage is not sensed, or the lamps malfunction, the red LED turns on continuously and the system error alarm sounds for ten seconds at a rate of ten beeps per second.
   f. If the proper dose is achieved within the appropriate time limit, the UV lamps stop flashing, the solenoid is pulsed to unlock the carriage, the green LED blinks continuously, the audible indicator sounds continuously for two seconds, and the cycle counter is pulsed.
5. The handle is then pushed forward by the patient to advance the third connector 56 and its holder into the second position adjacent to the second holder and connect the second and third connectors.
   a. The shuttle switch pulses the solenoid to lock the carriage in the forward, connected position.
   b. The green LED turns on and a two second, continuous tone is sounded.
   c. The continued forward motion of the handle mechanically releases the cover.
   d. The cover and port sensing switches remove power from the circuitry.
6. The cover is opened and the components are removed. The green LED turns on.

As noted above the logic portion of the functions are achieved by an ASIC (application specific integrated circuit). Such a circuit is can be obtained from different manufacturers such as the National Semiconductor Corp. by supplying the functions to be performed (i.e. logic charts represented by FIGS. 7-9) and the general circuit diagram such as FIG. 6.

The invention can be practised other than specifically as described without departing from the spirit or scope thereof.

What is claimed is:

1. In an improved electromechanical apparatus for breaking, forming and irradiating tubing connections for fluid flow for antimicrobial effect therein, the improvement comprising, in combination;

a housing having top and bottom portions removably attached to one another; u.v. irradiation means; and
electromechanical means in said housing for effecting said exchange and irradiation of said tubing connectors, said electromechanical means including means for forcing compliance with a predetermined sequence of steps to effect said exchange and irradiation by user of said apparatus.

2. The apparatus of claim 1 wherein all electronic components of said electromechanical means are contained in said top portion of said housing.

3. The apparatus of claim 1 wherein all of the electrical components of said electromechanical means are contained in said top portion so that said components will not be in the path of flow of any of said fluid which may escape said tubing connections.

4. Apparatus for breaking, forming and irradiating tubing connections for fluid flow for antimicrobial effect therein comprising:

a housing having top and bottom portions removably attached to one another; u.v. irradiation means; and electromechanical means associated with said housing for preventing operation of said apparatus when fluid may be leaked from said tubing connections, said electromechanical means including clamp sensing means for sensing the presence of a clamp.

5. The apparatus of claim 4 wherein all of the electrical components of said electromechanical means are contained in said top portion so that said components will not be in the path of flow of any of said fluid which may escape said tubing connections.

* * * * *